US010471471B2

(12) United States Patent
Hynynen et al.

(10) Patent No.: US 10,471,471 B2
(45) Date of Patent: *Nov. 12, 2019

(54) ULTRASOUND TRANSDUCER AND METHOD FOR MAKING THE SAME

(71) Applicant: SUNNYBROOK RESEARCH INSTITUTE, Toronto (CA)

(72) Inventors: Kullervo Hynynen, Toronto (CA); Junho Song, Toronto (CA)

(73) Assignee: SUNNYBROOK RESEARCH INSTITUTE, Toronto, ON (CA)

( * ) Notice: Subject to any disclaimer, the term of this patent is extended or adjusted under 35 U.S.C. 154(b) by 707 days.

This patent is subject to a terminal disclaimer.

(21) Appl. No.: 15/091,284

(22) Filed: Apr. 5, 2016

(65) Prior Publication Data
US 2016/0288168 A1    Oct. 6, 2016

Related U.S. Application Data

(63) Continuation of application No. 13/623,730, filed on Sep. 20, 2012, now Pat. No. 9,327,317.
(Continued)

(51) Int. Cl.
*A61N 7/02* (2006.01)
*H01L 41/29* (2013.01)
(Continued)

(52) U.S. Cl.
CPC .......... *B06B 1/0622* (2013.01); *A61B 8/4488* (2013.01); *A61N 7/02* (2013.01);
(Continued)

(58) Field of Classification Search
CPC .......................... H01L 41/0475; B06B 1/0622
See application file for complete search history.

(56) References Cited

U.S. PATENT DOCUMENTS 4,890,268 A * 12/1989 Smith .................. B06B 1/0629
310/334
5,381,067 A    1/1995 Greenstein et al.
(Continued)

FOREIGN PATENT DOCUMENTS

| JP | 6169298 | 4/1986 |
|---|---|---|
| JP | 09-084193 | 3/1997 |
| WO | 2006083539 | 8/2006 |

OTHER PUBLICATIONS

Song et al., Fabrication of one-dimensional linear diagnostic and therapeutic high intensity focused ultrasound (HIFU) phased-arrays using lateral-mode coupling method, Proceedings from the 2010 IEEE International Ultrasonics Symposium (2010).
(Continued)

*Primary Examiner* — Thomas M Dougherty
*Assistant Examiner* — Karen B Addison
(74) *Attorney, Agent, or Firm* — Hill & Schumacher

(57) ABSTRACT

The present application provides a multilayer lateral mode coupling method for phased array construction and transducer devices built accordingly. This disclosure describes and demonstrates that the electrical impedance of a phased array can be substantially reduced and readily controlled to be close to the source impedance. The fabrication process is relatively simple and inexpensive. In addition, the elements are robust for use in 1.5, 2, 3 or other dimensional configurations, over an extended period of operation, without structural failure, and providing a high power output required for imaging and/or medical therapy applications.

10 Claims, 14 Drawing Sheets

Related U.S. Application Data

(60) Provisional application No. 61/536,636, filed on Sep. 20, 2011.

(51) Int. Cl.
  *B06B 1/06* (2006.01)
  *A61B 8/00* (2006.01)
  *H01L 41/047* (2006.01)

(52) U.S. Cl.
  CPC .......... *H01L 41/0475* (2013.01); *H01L 41/29* (2013.01); *Y10T 29/49005* (2015.01)

(56) References Cited

U.S. PATENT DOCUMENTS

| | | | |
|---|---|---|---|
| 5,415,175 A | | 5/1995 | Hanafy et al. |
| 5,620,479 A | | 4/1997 | Diederich |
| 5,823,962 A | | 10/1998 | Schaetzle et al. |
| 5,938,612 A | * | 8/1999 | Kline-Schoder ........ B06B 1/064 310/334 |
| 6,761,692 B2 | * | 7/2004 | Angelsen ............... B06B 1/0688 310/334 |
| 7,876,027 B2 | * | 1/2011 | Cochran ................. B06B 1/064 310/334 |
| 9,327,317 B2 | * | 5/2016 | Hynynen ............... B06B 1/0622 |
| 2002/0073781 A1 | | 6/2002 | Hashimoto et al. |
| 2002/0157472 A1 | | 10/2002 | Stephens et al. |
| 2003/0107303 A1 | | 6/2003 | Mohr, III et al. |
| 2004/0054287 A1 | | 3/2004 | Stephens |
| 2007/0167764 A1 | | 7/2007 | Hynynen |
| 2007/0222339 A1 | * | 9/2007 | Lukacs ................. B06B 1/0622 310/335 |

OTHER PUBLICATIONS

European Search Report in European Application No. 12834082.5-1559, dated Sep. 8, 2015.

Patent Cooperation Treaty, International Search Report for PCT/US2012/056393, Nov. 20, 2012.

\* cited by examiner

ULTRASOUND TRANSDUCER AND METHOD FOR MAKING THE SAME

RELATED APPLICATIONS

This application is a non-provisional of and claims the benefit of U.S. Application No. 61/536,636, filed on Sep. 20, 2011, which is incorporated herein by reference.

TECHNICAL FIELD

The present disclosure relates to the design and construction of ultrasound transducers and arrays of multiple transducers.

BACKGROUND

Ultrasound offers a fast, non-invasive, and cost-effective imaging and treatment modality in modern medical practices. Its applications have been rapidly growing with the advances of phased array fabrication and electronics technologies. Ultrasound waves and ultrasound energy fields are projected from an ultrasound transducer into a volume undergoing imaging or therapy. A transducer operates on the principle of converting input electrical driving signal energy to output ultrasound energy because the material of which the transducer is made undergoes mechanical dimensional changes commensurate with the input driving electrical signal. Also, depending on the application, a transducer can convert incident ultrasound energy into electrical energy that can be measured, through a converse mechanical to electrical transduction process whereby dimensional compression by the incident acoustic waves excites or induces an electrical response in the material of the transducer. Typical materials used to manufacture ultrasound transducer elements are piezoelectric crystal materials such as lead zirconate titanate (PZT) and similar materials.

In transmission mode, the ultrasound energy is emitted from a face of a transmitting transducer and propagates according to the known laws of acoustic energy propagation in the medium of choice, typically a fluid or viscoelastic or other medium permitting propagation of ultrasonic sound waves. The tissue of a patient undergoing imaging or therapy with a transducer device or array is sometimes approximated as a viscoelastic fluid and has acoustic parameters such as sound speed and absorption coefficients that can be determined and affect the way in which the ultrasound waves move through the body of the patient.

A plurality of ultrasound sources or transducer elements may be grouped into arrays, which have been produced in one and two dimensions. By controlling the electrical drive signals to each of (or groups of) the ultrasound elements of the array, the resultant emitted sound fields from the array as a whole can be controlled and directed in space and time. Both the amplitude and the phase of the electrical driving signal applied to elements of an array are controlled, at the individual element level, using a computer controlled driving circuit.

When the size of a transducer element is sufficiently small it acts as a point source of ultrasound when observed from a relative distance away from the transducer. The so-called far-field behavior of an ultrasound array is often approximated by considering the cumulative effect from each member transducer of the array. For arrays of many transducer elements the principle of superposition generally applies, at least as a first approximation in linear systems, whereby the total ultrasound field is derived by additively summing the effect of the individual elements of the array to obtain a net field of the total array at any instance in space and time. Phased arrays therefore allow an ultrasound beam to be created (having a given spatial distribution) and allow for electronically steering and focusing the beam in a target volume without the need for mechanical means to steer or reposition the transducer. One can precisely and rapidly control acoustic power deposition at multiple locations using phase aberration correction algorithms in order to steer and focus the beam through different tissue layers, such as fat and muscles. Taking advantage of these unique capabilities, fast volumetric imaging and coagulation of cancer tissue seated deeper in the body can be readily performed.

The construction of phased arrays that allow flexible and precise beam formation and steering can involve complex and sophisticated design and manufacturing steps. One design criteria that is sometimes used in ultrasound array design is that the center-to-center spacing (or pitch) between the array elements should be equal to or smaller than half the wavelength to avoid unwanted secondary peaks, such as grating lobes. However, with increased frequency (i.e., reduced wavelength) and a change in array configuration from one dimension to two, the phased array will have an increased number of small elements. A consequence of the small element size is not only the increased complexity of electrical connections to the individual elements but also increased electrical impedance of the elements.

The large electrical impedance of the small array elements can result in an electrical impedance mismatch between an RF driving system (source), generally 50 W, and the array elements. In diagnostic phased arrays, this impedance mismatch causes low acoustic power output in the transmit mode, and consequently poor sensitivity and signal-to-noise ratio (SNR) on the receive mode. Similarly, for high power therapeutic arrays, it can result in poor electrical-to-acoustic power conversion. The traditional solution for the problem is to employ an electrical impedance matching circuit for each element. Since this is accompanied by high manufacturing cost, the traditional method is not generally ideal or efficient for a phased array with a large number of elements. For this reason, the elements are usually designed to have electrical impedances close to the source impedance in order to maximize power transmitted to the elements without using matching circuits.

Attempts have been made to reduce the electrical impedance of array elements instead of using electrical matching circuits. Some methods seek to stack multiple layers (N layers) of piezoelectric material using the thick film process of tape casting to decrease the element's total electrical impedance by a factor of $N^2$. However, the manufacturing process for this method is complicated and expensive. Similarly, bonded multilayer ceramics and composites using a dice-and-fill method may sometimes improve the electrical power transmitted to the array elements. Although the complexity of the fabrication process may be improved, there arise other problems with alignment and delamination of the bonding layers.

An improved transducer design and method of making such transducers and arrays of the same are needed and useful in at least the fields of ultrasonics, medical imaging, ultrasound therapy, and other medical and industrial applications of acoustic transducer technology.

SUMMARY OF THE INVENTION

Aspects of the present disclosure are directed to a multi-layer lateral-mode coupling method for phased array construction. The fabrication process is simple and inexpensive and the elements are robust for use over an extended period of operation without any structural failure. In addition we introduce an array structure that will allow high power output required for therapy delivery.

Further aspects of the present apparatus and method are directed to a multilayer lateral-mode coupling method for phased array construction. In some embodiments, the electrical impedance of a phased array constructed using this method is substantially reduced relative to existing methods, and readily controlled to be close to the source impedance so that the array can be driven without using electrical matching circuits. In some aspects, a multilayer transducer element is driven in the lateral mode of a piezoelectric ceramic plate and an array of such elements is designed and manufactured for use, e.g., in the field of medical ultrasound.

In some aspects the total electrical impedance of an N-layer lateral mode transducer is $(Nt/w)^2$ times smaller than for a single layer transducer driven in thickness mode (where w is the width and t is the thickness of the array element).

Various embodiments may reduce the manufacturing cost associated with diagnostic and therapeutic phased arrays. Some embodiments may reduce or eliminate the need for electrical impedance matching circuits in the array design. High power therapeutic arrays may become more practical or possible because the electrodes are constructed so as to transfer heat away from the array elements, and because the present method of lateral mode excitation avoids delamination of the transducers.

In some embodiments, in the case of imaging arrays, high frequencies, up to and beyond 100 MHz, may be obtained using the presented techniques.

An embodiment is directed to a method for fabricating an acoustic array of transducer elements, comprising providing a plurality of acoustic transducer elements, each having a respective plurality of dimensions defining its spatial extent, including a first dimension along a first axis along which said element radiates acoustic energy when excited by an electrical driving signal; mechanically arranging said plurality of transducer elements along at least a first axis substantially perpendicular to said first axis in an active face of said array; providing a plurality of conducting foils acting as electrodes to deliver electrical driving signals to the transducer elements, said conducting foils interspersed between said plurality of acoustic transducer elements such that an adjacent pair of transducer elements share a same electrode lying between said pair of adjacent transducers; and driving said plurality of transducer elements with electrical driving signals through said conducting electrodes.

Another embodiment is directed to an acoustical array device, apparatus or system comprising a plurality of acoustic transducer elements; each transducer element comprising an element of a multi-element array of transducers; each transducer element being mechanically responsive, along a first axis, to a received electrical driving signal, so as to vibrate along said first axis upon application of the received electrical driving signal by a pair of electrodes electrically coupled to corresponding opposing faces of said transducer along a second axis, said second axis being substantially normal to said first axis; and wherein said plurality of transducer elements are arranged with respect to one another in a face of said array so that a common electrode disposed between two adjacent transducer elements is shared between said two adjacent transducer elements and acts as one or said pair of electrodes to each of said adjacent transducer elements.

BRIEF DESCRIPTION OF THE DRAWINGS

For a fuller understanding of the nature and advantages of the present concepts, reference is made to the following detailed description of preferred embodiments in connection with the accompanying drawings, in which.

DETAILED DESCRIPTION

Figure 1:
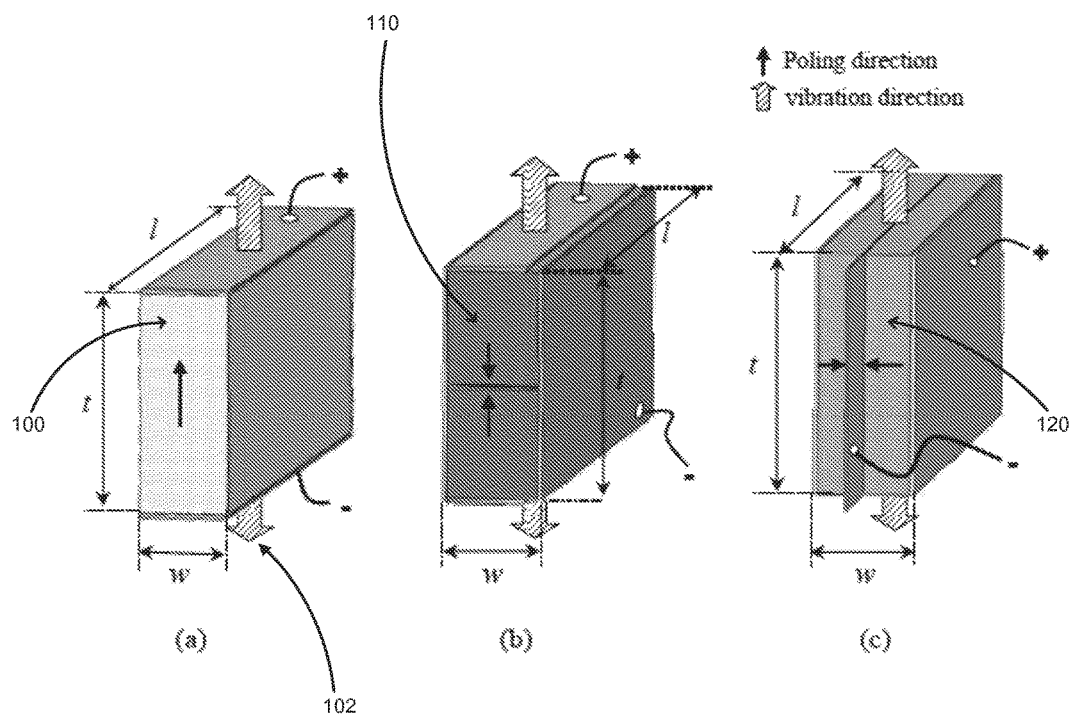
FIG. 1 illustrates exemplary schematic diagrams of piezoelectric ceramic PZTs driven in thickness mode and lateral coupling mode.

As discussed above, it is useful to reduce the electrical impedance of a phased array and control said electrical impedance to be close to the source impedance so that said array can be driven without using electrical matching circuits. It is also desired to facilitate heat removal from a region of a transducer or transducer array to keep the same within acceptable operating temperature limits during operation, especially at relatively high powers or for relatively long operating times. This is especially helpful in situations where the physical characteristics of the transducer or array or other components may be adversely affected or altered or detuned by an unwanted or unaccounted rise in temperature during operation.

Some or all of the present inventors and/or applicants have presented applications for improved transducer device designs and manufacture of the same, which are hereby incorporated by reference. For example, see, US Pat. Pub. No. 2007/0167764 A1, from U.S. patent application Ser. No. 11/600,301 and Provisional Appl. No. 60/736,713, the contents of which are hereby incorporated by reference.

The present disclosure provides concepts for a design, fabrication and method of use and driving of a multilayer lateral mode transducer element (and/or array) which can be used in diagnostic and HIFU phased array construction. The present systems and method provide a highly efficient and easy way to reduce the large electrical impedance of an array element with small width-to-thickness ratio along with temperature reduction for high-power applications.

As exemplary embodiments, and to validate the lateral coupling method, we describe below by way of illustration, extension of which will be apparent to those skilled in the art, the fabrication and performance of a one-dimensional linear 32-element (770 kHz) imaging and a 42-element (1.45 MHz) high intensity focused ultrasound (HIFU) phased array. The present discussion and examples showing the benefit of the present lateral mode coupling technique. Both the arrays in the present example have been tested by the present inventors and were driven without electrical matching circuits. This reduced the amount of time to fabricate the arrays as well as the fabrication cost and complexity. Further reduction of the electrical impedance can be easily achieved by adding more layers in the design.

In a preferred embodiment, the present multilayer transducer element is driven in lateral mode of a piezoelectric ceramic plate. To maximize its performance, we constructed the arrays from a soft PZT-5 ceramic plate, and took advantage of its higher dielectric constant ($\varepsilon^T$), coupling factor ($k_{31}$), and electromechanical constant ($d_{31}$) than for the hard PZT ceramic plates (e.g. PZT-4). Table 1 shows the material properties of a hard PZT-4 and soft PZT-5 ceramics. Of course, these properties are merely exemplary and intended to illustrate the present example, and are not intended to be limiting or exhaustive of the possible range of properties that may be employed within the present scope.

TABLE 1

| Parameter | PZT-4 | PZT-5 |
|---|---|---|
| Relative dielectric constant | 1550 | 3900 |
| Dielectric dissipation factor, tan δ | 0.004 | 0.018 |
| Curie Temperature (° C.) | 250 | 210 |
| Charge constant, $d_{33}$ (pC/N) | 250 | 690 |
| Charge constant, $d_{31}$ (pC/N) | −125 | −340 |
| Coupling factor, $k_{33}$ | 0.7 | 0.80 |
| Coupling factor, $k_{31}$ | 0.35 | −0.46 |
| Density (g/m³) | n/a | 7.95 |
| Quality factor, Qm | 400 | 46 |

Since the PZT-5 has higher $k_{31}$ and $d_{31}$ than the PZT-4, it offers higher transmitting acoustic power output and receiving sensitivity in the lateral direction. Its high dielectric constant offers lower electrical impedance so that it requires less effort to reduce the electrical impedance than fabricating the transducers with a hard PZT. The present results demonstrated that adequate power outputs even for HIFU purposes were achieved with the softer material although it is not commonly used for high power applications.

In some aspects, the present lateral mode coupling technique facilitates ease of fabrication and reduction of the electrical impedance of the present devices. Since we started with large ceramic plates and bonded them under microscope in the beginning of the fabrication, we did not experience any misalignment problems. In some embodiments, we controlled the bonding layer thickness to be equal or less than about 25 μm using 20 μm thick silver foils thus decreasing the mechanical compliance and coupling losses caused by thick bonding layers. The bonding layer thickness can be further reduced using a thinner intermediate conductive foil. Additionally, since the two transducer layers always were vibrating in the same manner, either compressing or expanding, no delamination problem was observed for two-layer lateral mode transducers.

For a multilayer, piezoelectric ceramic array element driven in lateral mode, it is possible to minimize the electrical impedance of the element by electrically connecting multiple transducer layers in parallel and driving them in unconventional mechanical vibration mode, the lateral mode.

FIG. 1 shows an example of three different array element configurations; (a) a single layer transducer, (b) a two-layer transducer, and (c) a two-layer lateral mode transducer. Specifically, FIG. 1(a) shows a single layer PZT 100 driven in thickness mode (indicated by the vibration direction arrows 102). FIG. 1(b) shows a two-layer PZT 110 driven in thickness mode. FIG. 1(c) shows a two-layer lateral mode PZT 120. The overall dimensions are the same for the three PZTs. The polarity of the PZT crystals is indicated by the poling direction arrows drawn on the faces of the PZT elements The transducers shown in FIGS. 1 (a-b) will be driven in thickness mode while the two-layer lateral mode transducer (FIG. 1(c)) will be used to vibrate in lateral mode. The elements of the array, including transducer layers, are poled in the thickness direction indicated by the small arrows. For the simplicity of analysis, it is assumed that there are no mechanical and electrical losses on the cable and piezoelectric transducer. The single layer transducer (FIG. 1(a)) with thickness t, width w, and length l has the clamped capacitance $C_0$, given by $$C_0 = \varepsilon_0 \varepsilon_T A_0 / t,$$

where $A_0$ (=l×w) is the electrode area, $\varepsilon_0$ is the permittivity of free space (8.854×10$^{-12}$ F/m), and $\varepsilon^T$ is the relative clamped dielectric constant of the piezoelectric ceramic transducer. The electrical impedance, $Z_0$, is inversely proportional to the capacitance. The resonant frequency of the single layer transducer is governed by the thickness t. The width w is less than or equal to half the wavelength.

FIG. 1(b) shows a two-layer transducer driven in thickness mode with a layer thickness of t/2. The overall dimensions are the same as the single layer transducer. With the same transducer thickness t, the resonant frequency would be substantially the same as that of the single layer transducer. The inner electrode between the transducer layers is connected to ground and the outer electrode is connected to the signal line. The total clamped capacitance, $C_T$, and electrical impedance, $Z_T$, of the two-layer transducer are $$C_T = \varepsilon_0 \varepsilon^T A_T / t_T = 2\varepsilon_0 \varepsilon^T (l \times w)/(t/2)$$

$$= \varepsilon_0 \varepsilon^T (2A_0)/(t/2)$$

$$= 4C_0$$

$$Z_T = \tfrac{1}{4} Z_0$$

where the total surface area of the electrodes, $A_T$, doubles and the element thickness, $t_T$, decreases by half compared to the single layer transducer. As a result, the overall electrical impedance decreases by a factor of four.

In a two-layer lateral mode transducer (FIG. 1 (c)), the transducer is driven at a resonant frequency of the lateral mode instead of the thickness mode. When an electric field is applied to the transducer, the two layers simultaneously vibrate in the lateral direction with the same phase, both expanding and contracting. Similarly to the two-layer transducer shown in FIG. 1(b), the inner electrodes of the layers are connected to ground, and the outer electrodes are connected to the signal so the electrical connection of the layers is made in parallel. Compared to the single array element driven in thickness mode, the fundamental difference in the construction of the two-layer lateral mode element is that the thickness of each layer is half the width of the single layer element while the width of the layer is the same as the thickness of the single element. Therefore, the total electrode area, $A_L$, and layer thickness, $t_L$, of the two-layer lateral mode transducer are $$A_L = 2(l \cdot t),$$

$$t_L = w/2.$$

The total clamped capacitance, $C_L$, and electrical impedance, $Z_L$, are $$C_L = \varepsilon_0 \varepsilon^T (A_L)/t_L$$
$$= 2\varepsilon_0 \varepsilon^T (l \cdot t)/(w/2)$$
$$= 4 C_0 (t/w)^2,$$

$$Z_L = \frac{1}{4} \frac{1}{C_0} \left(\frac{w}{t}\right)^2$$
$$= \frac{1}{4} Z_0 \left(\frac{w}{t}\right)^2$$
$$= Z_T \left(\frac{w}{t}\right)^2.$$

where the width-to-thickness ratio, w/t, is always smaller than 1 when the $\lambda/2$ center-to-center spacing design rule is used in the phased array fabrication. Therefore, the electrical impedance of the two-layer lateral mode transducer will be lower than both the single layer and the two-layer transducer driven in thickness mode. The resonant frequency of the transducer will be the same or close to that of the single layer transducer since they have the same transducer thickness t.

The present illustrative examples are provided as guides to those skilled in the art and are not limiting in their express or implied description of the embodiments covered by this disclosure or invention. Other geometries, dimensions and material properties and driving signals may also be used in the present context without loss of generality or understanding.

Table 2 shows overall comparisons of the electrical impedance between n-layer transducers driven in thickness and lateral modes in an exemplary embodiment.

TABLE 2

| element type/ coupling mode | Overall element area | Overall element thickness | layer thickness | Capacitance | Impedance |
|---|---|---|---|---|---|
| single layer/ thickness mode | $l \cdot w$ | t | t | $C_0 = \varepsilon \frac{l \cdot w}{t}$ | $Z_0 \propto 1/C_0$ |
| n-layer/ thickness mode | $n(l \cdot w)$ | t | $\frac{t}{n}$ | $n^2 C_0$ | $\frac{Z_0}{n^2}$ |
| n-layer/ lateral mode | $n(l \cdot t)$ | t | $\frac{w}{n}$ | $(n^2) C_0 \left(\frac{t}{w}\right)^2$ | $\frac{Z_0}{n^2}\left(\frac{w}{t}\right)^2$ |

The direct comparison shows that the total electrical impedance of an n-layer lateral mode transducer is $(nt/w)^2$ times smaller than for a single layer transducer driven in thickness mode.

In order to compare the performance thickness and lateral mode transducers one element with identical dimensions was manufactured with each method. The overall dimensions were the same for both the transducers: the thickness t is 2.4 mm, width w was 0.83 mm, and length l was 20 mm. A single layer thickness of the two-layer PZT-5 transducer was 0.4 mm so the resulting width-to-thickness ratio was 0.33. The bonding layer with the conductive epoxy and silver foil was approximately 0.05 mm thick We also constructed two one-dimensional linear phased array prototypes for imaging and therapeutic applications from piezoelectric ceramic plates. Table 3 shows the design parameters of the two phased arrays.

TABLE 3

|  | Imaging phased array | HIFU phased array |
|---|---|---|
| Transducer material | PZT-5 | PZT-5 |
| Frequency | 750 ± 50 kHz | 1.5 ± 0.1 MHz |
| Coupling mode | Lateral mode | Lateral mode |
| # of array elements | 32 | 42 |
| # of layers | 2 | 2 |
| Single layer thickness (mm) | 0.4 | 0.2 |
| Bonding layer (mm) | 0.025 | 0.025 |
| Assembled array element size (mm) | 20 (l) × 0.83 (w) × 2.4 (t) | 14 (l) × 0.43 (w) × 1.2 (t) |
| Width-to-thickness ratio (w/t) (excluding the bonding layer) | 0.33 | 0.33 |

Both arrays were fabricated with two-layer lateral mode transducer elements. The imaging phased array consists of 32 elements with a center frequency of 750 kHz. It is designed for transcranial imaging applications. Each element is 2.4 mm thick, 20 mm long and 0.83 mm wide. The 42-element high-intensity focused ultrasound (HIFU) phased array was constructed for endocavitary applications, such as for prostrate tumor ablation. The elements have a center frequency of 1.5 MHz and dimensions of 14 mm (l)×0.43 mm (w)×1.2 mm (t).

Figure 2:
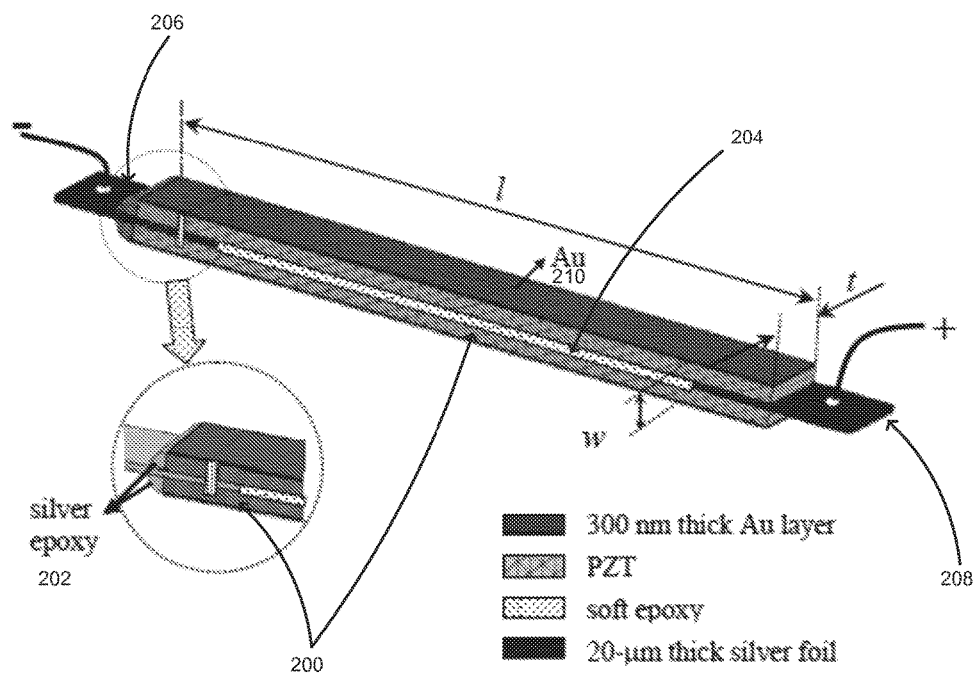
FIG. 2 illustrates an exemplary schematic diagram of a single two-layer PZT with shared electrode construction.

FIG. 2 illustrates placement of a plurality of layers (two shown) of PZT elements 200 having conducting (e.g., silver) epoxy termination points 202 and separated by a soft epoxy medium 204. A pair of conducting (e.g., silver) electrodes 206, 208 are disposed at opposing ends of the assembly to provide driving signals thereto. The PZT elements 200 are arranged in a pair of substantially planar parallel plates as shown, sandwiched between thin sheets of highly conducting (e.g., gold, Au) foils 210. The PZTs 200 driven in their lateral mode. The overall thickness of the two-layer PZT 200, w, is less than half the wavelength at a given operating (center) driving frequency according to some embodiments.

Stacked (rows) assemblies of such elements adjacent to one another or packed assemblies (rows and columns, grids, randomly placed elements, radially placed elements, etc) can be formed to make an overall two or three dimensional transducer array assembly. Some embodiments employ electrically driven sets of transducer elements as described herein so as to form a controllable ultrasonic field for use in hyperthermia or focused ultrasound or high-intensity ultrasound therapy systems. An array of such driven elements is used together, which presents a sound field in the ultrasonic range capable of affecting a desired thermal treatment of a patient suffering from a disease.

Diagnostic applications of the present PZT systems also exist. For example, a system can include an array of 32-elements or more for use as an imaging array. Yet other applications include a plurality (e.g., dozens or hundreds) of driven elements for use in an endocavitary high intensity focused ultrasound (HIFU) array, constructed using the lateral mode coupling method described above shows a schematic diagram of a single two-layer lateral mode transducer element according to an embodiment.

The basic fabrication process is the same for the imaging and HIFU phased arrays. For example, in the first step of the imaging phased array fabrication, two 70 mm×20 mm PZT-5 plates (e.g., TRS610HD, TRS Ceramics, State College, Pa., USA) with a thickness of 0.2 mm were bonded with soft epoxy (301, Epoxy Technology®, Billerica, Mass., USA). Before bonding the two PZT-5 transducers, small pieces of 20 mm thick silver foils (e.g., GoodFellow, Oakdale, Pa., USA) are sandwiched between the two transducers on each side and electrically connected to the inner electrodes of the two transducers using silver epoxy (e.g., GPC 251, CreativeMaterials, Tyngsboro, Mass., USA). In the present example, relatively small sections of the foils between the transducers were used to make the electrical connection to reduce or eliminate problems caused by adding the silver foils, such as mechanical compliance changes. The foils are also used to bridge the electrical connection between the elements and connector. In the bonding processes, a mechanical clamp was used to compress the two transducers to minimize excessive bonding material and to control the overall bonding layer thickness to be the same as that of the silver foil. In one embodiment, approximately 2 mm of silver foil is sandwiched between the transducers with an additional 1 mm left exposed for wire connection.

The inner electrode may be connected to the signal line (+), and another set of electrodes on the top and bottom to ground (−). The conductive epoxy (e.g. silver epoxy) may be applied to only one of the silver foils and connected to the top and bottom electrodes for the ground connection. Then, as shown in the figure, the silver foil connected to the ground is disconnected from the inner electrodes by dicing through the bonded transducers deep enough to cut the sandwiched silver foil at 1 mm from the transducer edge. The kerf may be filled with the soft epoxy and 300 nm thick gold was evaporated onto the surface of the transducer. Individual elements are diced to 2.4 mm long from the fabricated 70 mm long, 20 mm wide, two-layer PZT-5 plates. Custom-designed, 1 m long coaxial cables (e.g., Precision Interconnect, Berwyn, Pa., USA) may be used to make electrical connection between the element and a ZIF connector (e.g., ITT Cannon, Shakopee, Minn., USA).

Before the final assembly process, the silver foils are coated with approximately 20 mm thick Parylene and thin layer of the soft epoxy to prevent from short circuits between adjacent array elements. Then, the individual elements may be bonded using silicone to minimize mechanical coupling between the elements. After finishing the assembly, the overall center-to-center spacing was measured under a microscope to be equal to or smaller than half the wavelength in water. A 5 cm thick backing material (e.g., PZT-4 powder/soft epoxy=2:1) is applied on the backside of the phased array. A 10 mm thick Parylene layer may be coated on the array surface to protect the elements from corrosion and mechanical damage.

Similarly, transducer elements of a HIFU array can be fabricated to be, e.g., 14 mm (l)×1.2 mm (t)×0.43 mm (w) using two 0.20 mm thick PZT-5 ceramics (e.g., TRS610HD, TRS Ceramics, State College, Pa., USA). The overall fabrication process can be the same as for the imaging array. Instead of using long coaxial cables, the elements are mounted on a printed circuit board (PCB) and individual electrical connection from the silver foils to the PCB board are made using 50 mm thick copper wires (e.g., California Fine Wire, Grover Beach, Calif., USA). No backing material is required for the array in some embodiments. These arrays and others can be constructed using the present lateral mode coupling method.

To validate the performance of the present lateral mode coupling method, the electrical impedance of the two-layer lateral mode elements can be measured using a network analyzer. A simple electrical impedance comparison between a single thickness mode and two-layer lateral mode transducers can be conducted by evaluating the measurement in air. Overall electrical impedance measurements for the imaging and HIFU arrays can be performed in degassed and deionized water.

Figure 3:
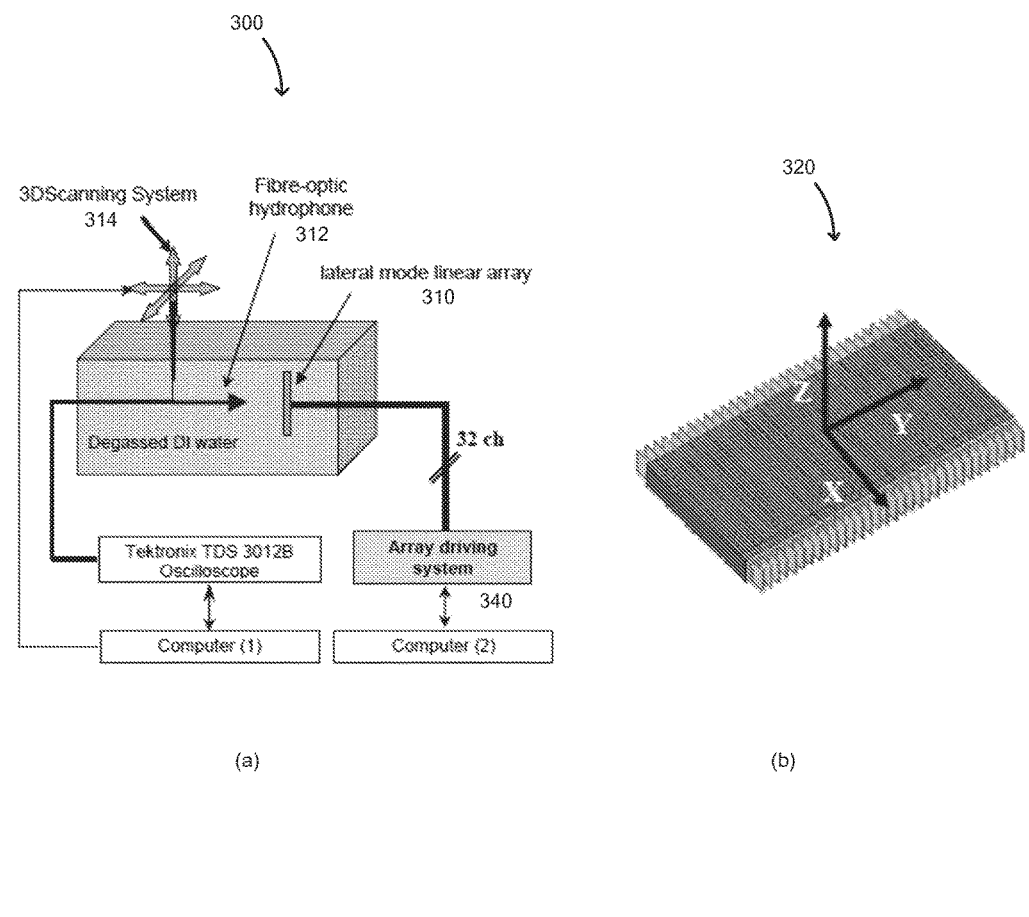
FIG. 3 illustrates an exemplary embodiment in which (a) an experimental setup for testing a 32 element imaging or a 42 element HIFU linear array, and (b) a Cartesian coordinate system with its origin at center of the array.

FIG. 3(a) shows the overall experimental setup 300 for the measurement of the pressure field radiated from the arrays 310. A tank holds the experiment and is lined with 1 cm thick rubber to minimize any acoustic reflections from the tank walls, and filled with degassed, deionized water (Resistivity >16 MΩ-cm), with dissolved oxygen level maintained below 1 ppm. The Cartesian coordinate system 320 used in the study is shown in FIG. 3(b). The origin of the coordinate system 320 is located at the center of the array 310 as shown, and the acoustic axis is parallel to the z axis. The ultrasound pressure fields radiating from the imaging and HIFU arrays are measured with a 40 mm long, 125 mm diameter planar fiber-optic hydrophone (e.g., Precision Acoustics, Dorchester, UK). A hydrophone 312 is moved with a 3-D scanning system 314 (e.g., Velmax Inc, Broomfield, N.Y., USA). A 42-element HIFU array 310 is then driven by an amplifier system 340 with a plurality (e.g., hundreds, dozens) of channels as needed. Of course, the present description is only exemplary, and those skilled in the art appreciate other ways of doing the same or substantially same or equivalent steps using various devices suited for the purpose.

A tone burst signal (e.g., PRF=330 kHz, duty cycle=1%) is used to drive each element of array 310. An electrical power of a 1 W/channel can be used to measure the radiated fields from the array in an example. The electrical-to-acoustic power conversion efficiency and maximum surface acoustic power of a single element of the HIFU phased array are measured using a scanning laser vibrometer (e.g., PSV-400-M2-20 20 MHz, Polytec, Tustin, Calif., USA).

Figure 4:
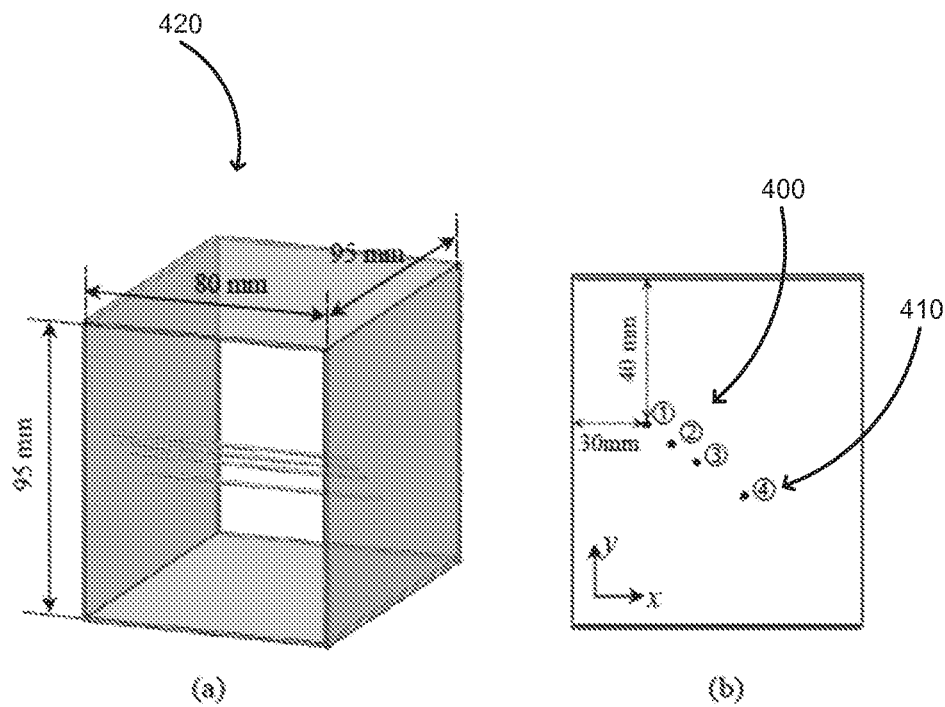
FIG. 4 illustrates an exemplary phantom and wires disposed in the phantom.

For single element experiments of the imaging array a pulser/receiver (e.g., Panametric 5072PR, Olympus, Waltham, Mass.) is used to transmit and receive the RF-signal. In these cases the received waveform is recorded using a digital oscilloscope. A commercial 32-channel imaging scanner (e.g., OPEN system, Lecoeur Electronique, Cheulles, France) is used in the experiments with the whole array. It is controlled via USB with custom-built C++ software running on a desktop computer. The OPEN pulser/receiver system excites the array with a 50 $V_{peak}$ and 12.5 ns long pulse, and received echo signals. The received echo signals is filtered using a zero-phase bandpass digital filter in MATLAB (e.g., Mathworks, Natick, Mass., USA). Then, a Hilbert transform is performed to obtain the envelope of the signals. The images are acquired with a ±30° serial scanning of the transmit and receive focus at half-degree increments in elevation angle. The beam is focused 60 mm from the transducer surface. Each scan line has a delay of 50 µs and 65 dB gain applied on all channels. The feasibility of imaging can be for example determined using a water phantom 420 with four 300 µm thick Nylon wires, as shown in FIG. 4. The first three wires are separated from each other by approximately 5 mm axially, 7 mm in elevation (8.6 mm on the diagonal). The fourth wire 420 is 10 mm axially, 13 mm elevation away from the third wire.

Again, none of the present detailed examples shall be considered limiting of the present invention, but rather as a particular example to aid the understanding of those skilled in the art.

Figure 5:
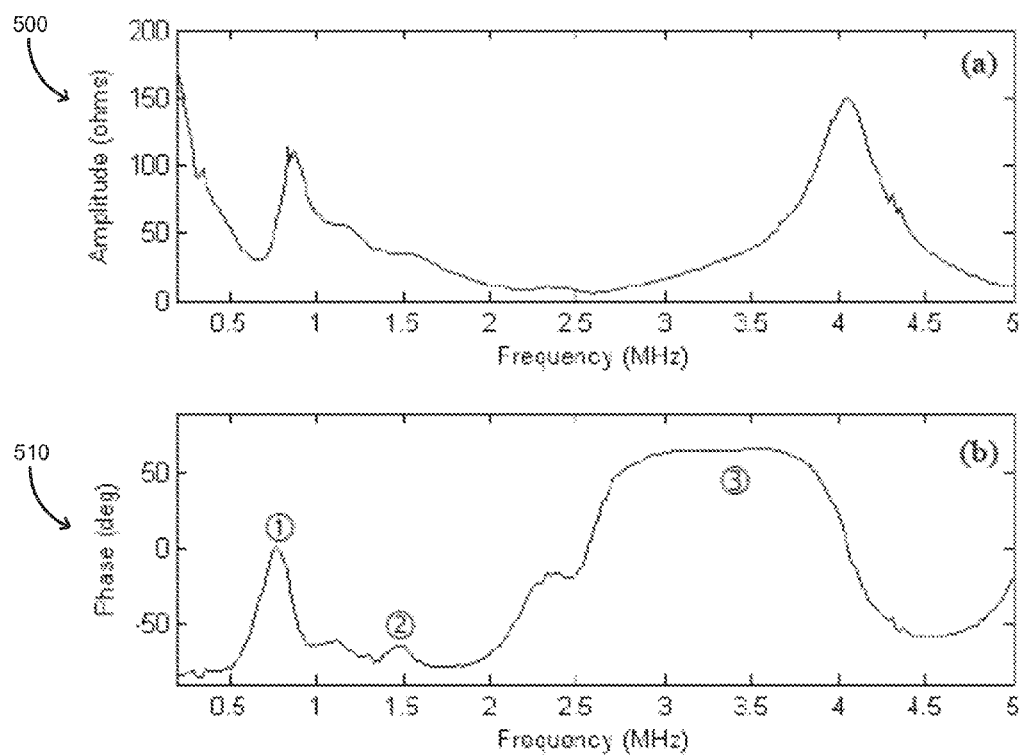
FIG. 5 illustrates an exemplary a graph comparing—the electrical impedance measurements between (a) a single layer transducer driven in thickness mode and (b) a two-layer transducer driven in lateral mode.

FIG. 5 illustrates a comparison of the electrical impedance measurements of a single layer transducer driven in thickness mode in an exemplary embodiment (FIG. 5(*a*)) and a two-layer lateral mode transducer (FIG. 5(*b*)). The impedance amplitude 500 in air at the maximum phase for the single layer thickness mode transducer was approximately 3000Ω at 840 kHz. The two-layer lateral mode transducer had an impedance amplitude of 73.3±1.2Ω at 770 kHz in air, which is 41 times smaller than that of the single layer with the same dimensions. This demonstrates the electrical impedance reduction without using a traditional method, such as employing an electrical matching circuit. In addition, the large electrical impedance of the small array element can be made to be close to the source impedance by controlling the number of layers and their thickness.

Figure 6:
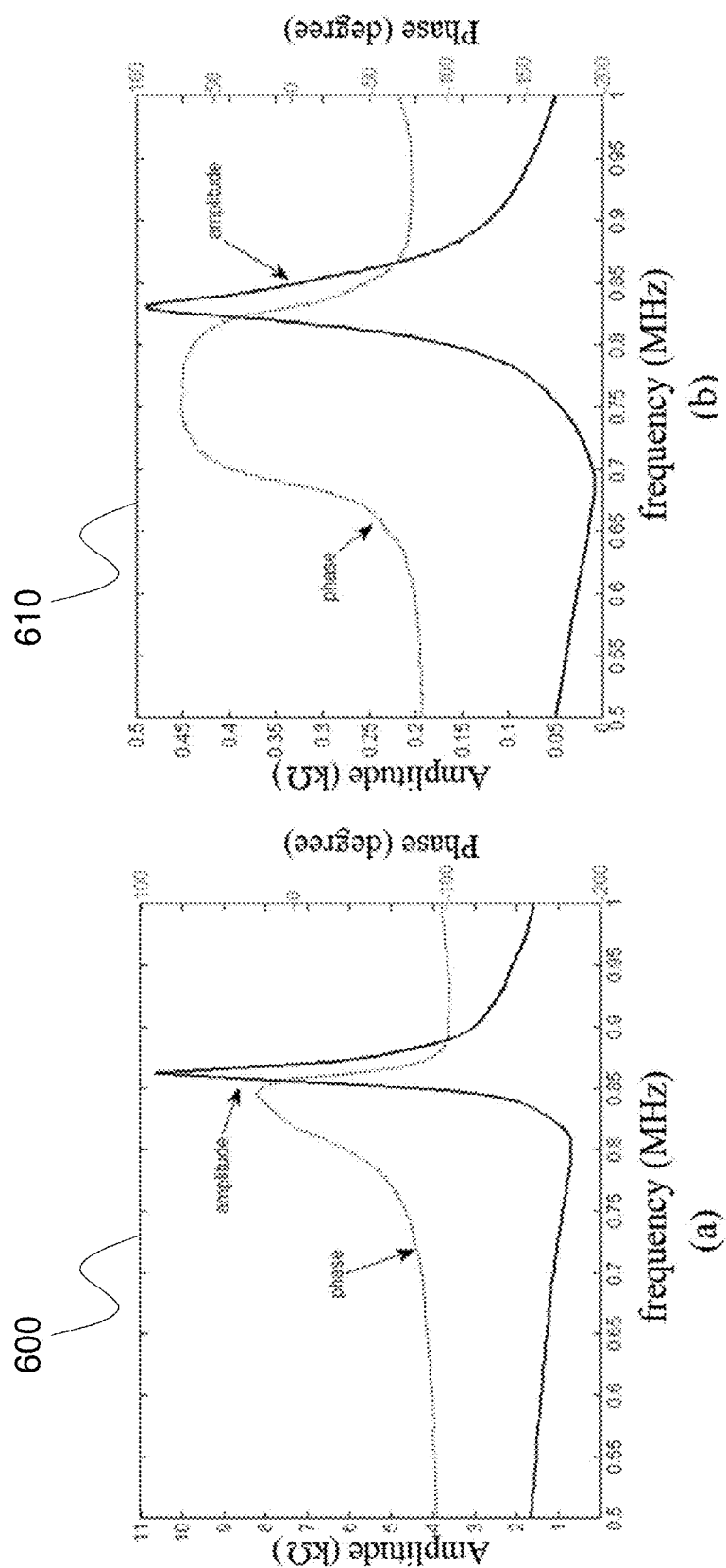
FIG. 6 illustrates some examples of the electrical impedance (a) amplitude and (b) phase measurements of the 32-element phased array elements in water; (1): lateral mode, (2): thickness mode corresponding to a two-layer array element, (3): thickness mode corresponding to a single layer transducer.

FIG. 6 shows an example of the electrical impedance plots of a fully assembled 32-element two-layer lateral phased array, measured in deionized water. The plots show the resonant frequencies at 770 kHz, 1.5 MHz and 3.4 MHz, respectively. The strong modes are shown at 770 kHz for the lateral mode of the element (600) and at 3.4 MHz for the thickness mode of the single layer transducer (610). Here, the thickness mode of the two-layer element at 1.5 MHz, was not as strong as the other two modes. The electrical impedance amplitude at 770 kHz is 58±3Ω at the maximum phase angle of −1.2°.

Figure 7:
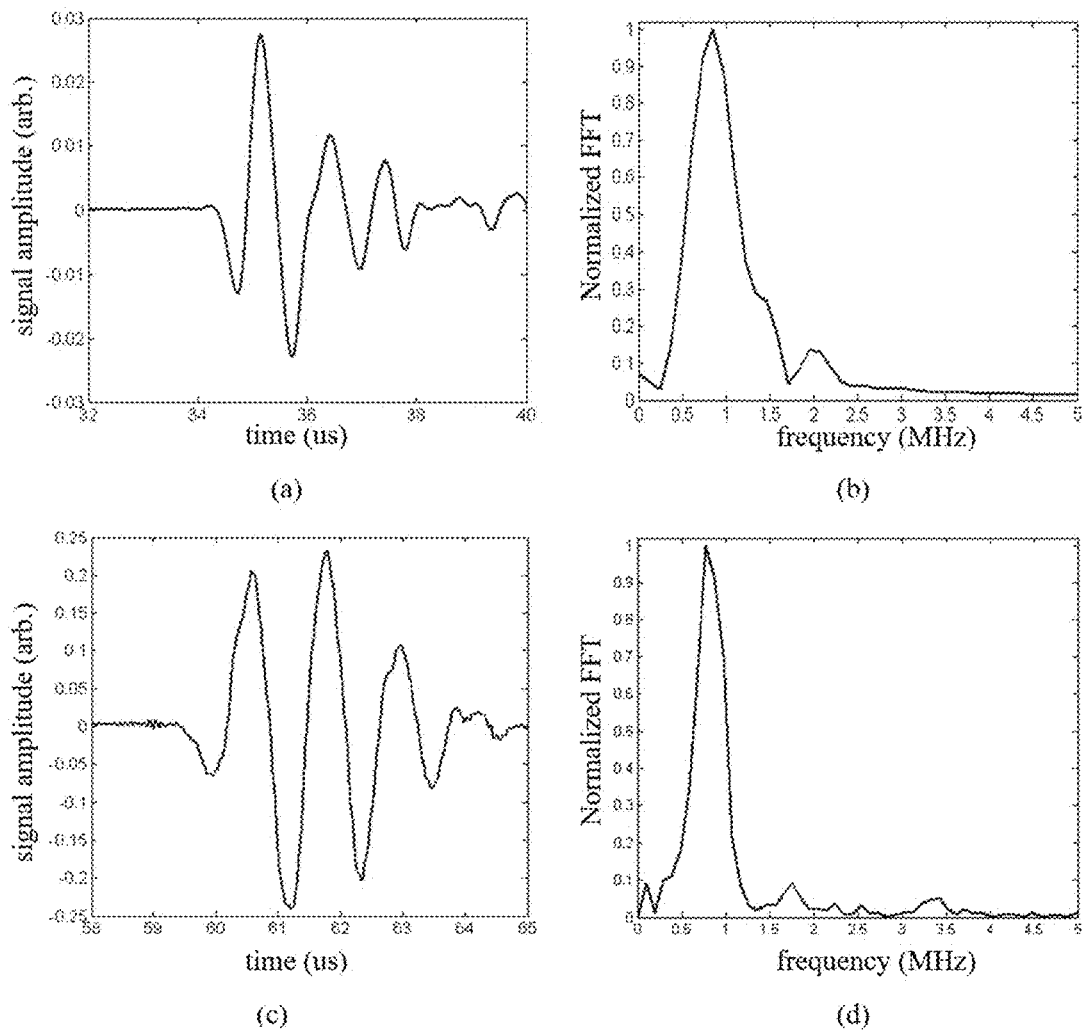
FIG. 7 illustrates an exemplary pulse-echo impulse response from the center element of the 32-element imaging array: (a-b) transmitted pulse measured and its corresponding normalized FFT, and (c-d) pulse-echo measurement and the corresponding normalized FFT of the waveform.

FIG. 7 shows a typical pulse-echo impulse response from the center element of the 32-element imaging phased array, reflected off a 5 cm thick acrylic plate from the array. FIGS. 7(*a*) and (*b*) show a transmitted pulse measurement and its corresponding normalized FFT. In the present embodiment, there was no matching circuit used to compensate electrical impedance mismatch. The −6 dB and −40 dB pulse lengths of the waveform are 1.6 µs and 3 µs, respectively, which correspond to approximately 1.2 and 2.3 cycles at 770 kHz. The corresponding normalized FFT (FIG. 7(*d*)) shows that the array has a center frequency of 770 kHz with −6 dB bandwidth of approximately 52%, measured at lower and upper frequencies of 612 kHz and 1.02 MHz. It should be appreciated that an electrical matching circuit may be employed in some applications, as deemed appropriate, but that the present designs and techniques can alleviate or eliminate the need for such circuits in some or many or all cases.

Figure 8:
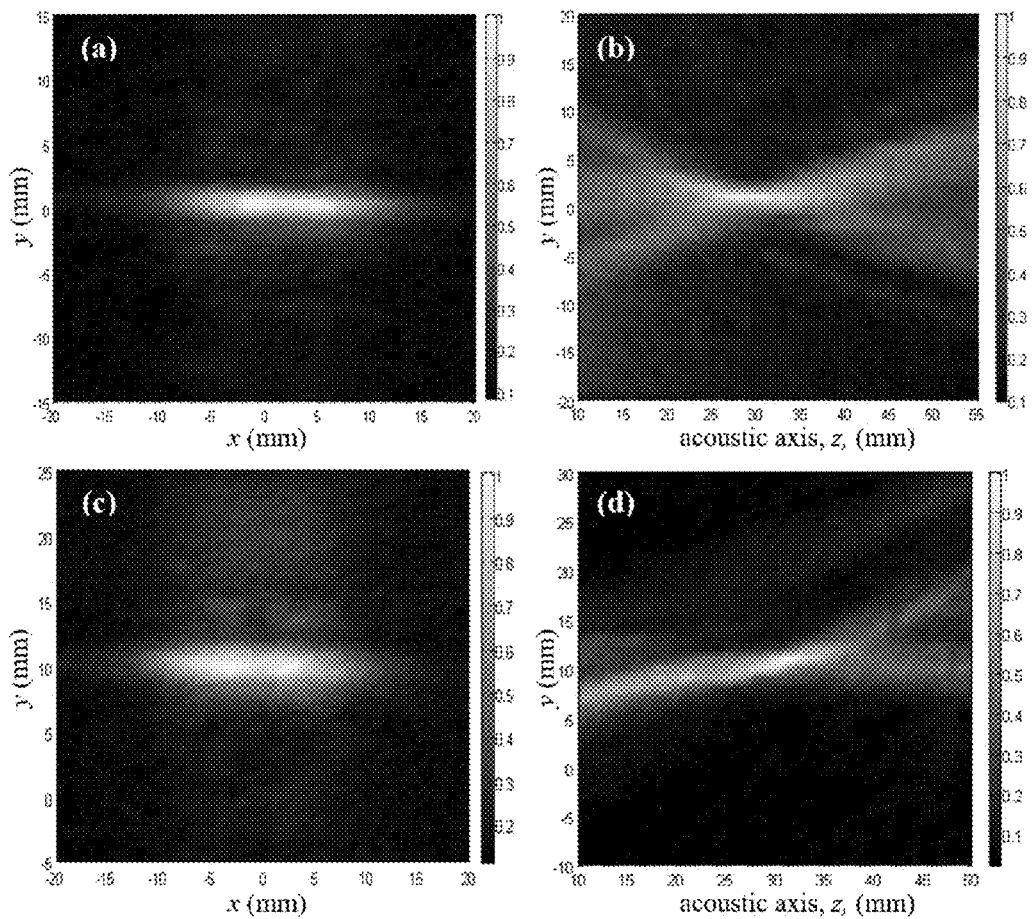
FIG. 8 illustrates exemplary normalized radiated pressure amplitude measurements in the XY and YZ planes when the array is focusing: (a-b) at (0, 0, 30) mm, and (c-d) at (0, 10, 30) mm.

FIG. 8 illustrates radiated pressure amplitude field measurements in the XY and YZ planes when the array was focusing at (0, 0, 30) mm and (0, 10, 30) mm. The field measurement shows a good steering capability of the 1D linear array.

Figure 9:
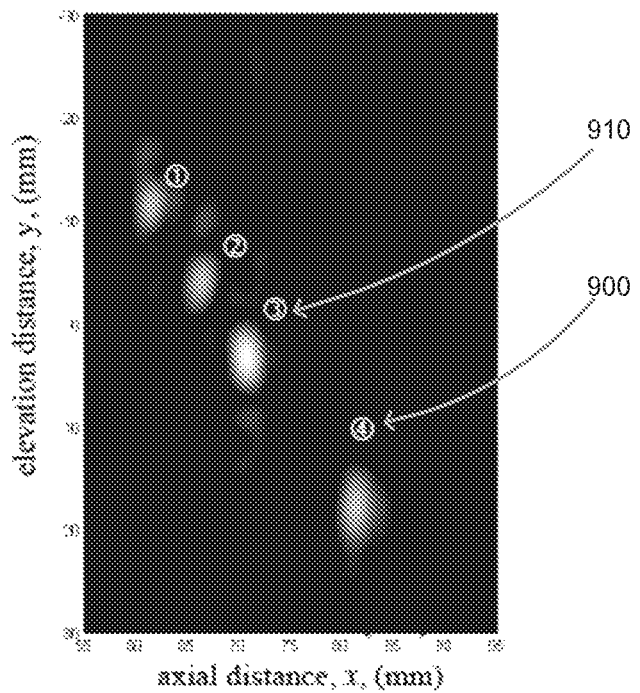
FIG. 9 illustrates a scanned image of the four nylon wires in a phantom.

FIG. 9 shows a scanned image of a bath containing four 300 mm thick Nylon wires as described earlier. The first three wires were shown to be approximately 5 mm axially, 7 mm in elevation apart each other, and the fourth wire 900 was seen at 10 mm axially, 13 mm elevation away from the third wire 910.

Similar laterally coupled transducers can be used to increase the bandwidth of the elements by making the transducer plates of different lengths such that they resonate at different frequencies such that a combined wideband operation is achieved.

Figure 10:
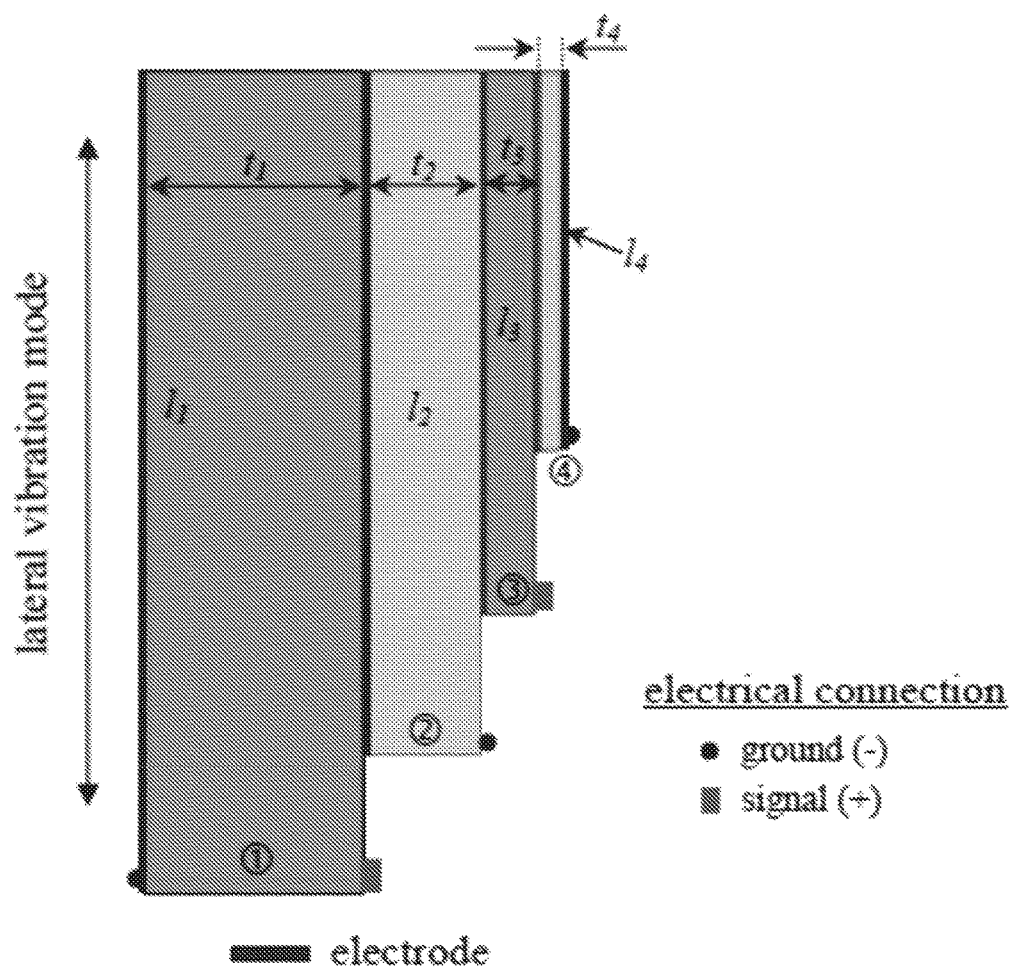
FIG. 10 illustrates an exemplary schematic diagram of a 4-layer PZT transducer with lateral vibration mode.
Figure 11:
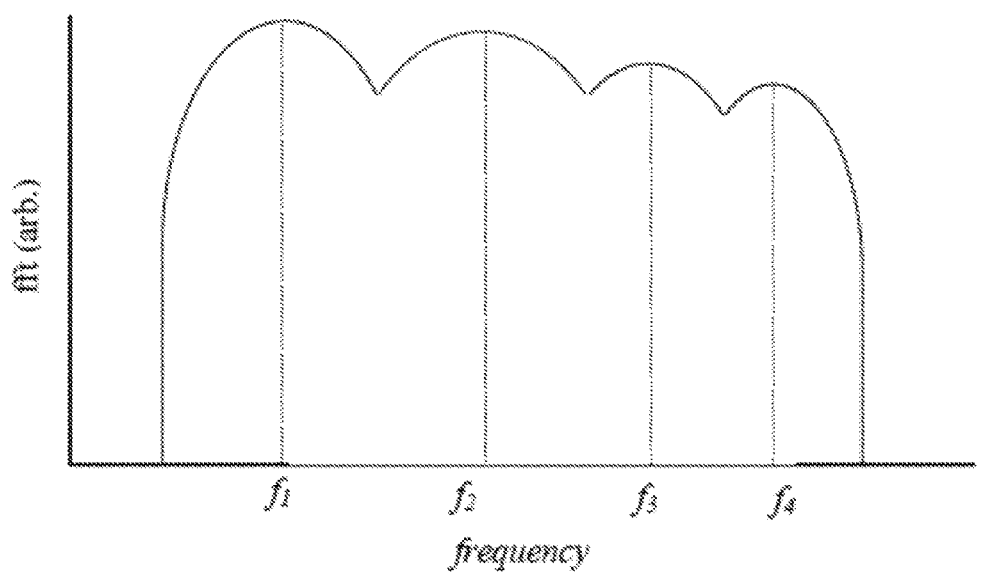
FIG. 11 illustrates a frequency spectrum of the 4-layer PZT transducer with lateral vibration mode.

An example of such a 4-layer PZT transducer with lateral vibration mode element is shown in FIG. 10, with its associated frequency spectrum in FIG. 11. In some aspects, 1-, 1.5- or 2-dimensional arrays can be formed from such elements according to the present teachings.

Dual-frequency or multi-frequency arrays 1200 can be formed by making the transducer elements from plates of two different lengths (e.g., 1202, 1204) so that they resonate at the desired frequencies corresponding to the lengths (or in the context of an array to the respective thicknesses of the transducer array elements). This is depicted for a pair of different sized elements in FIG. 12(*a*).

Figure 12:
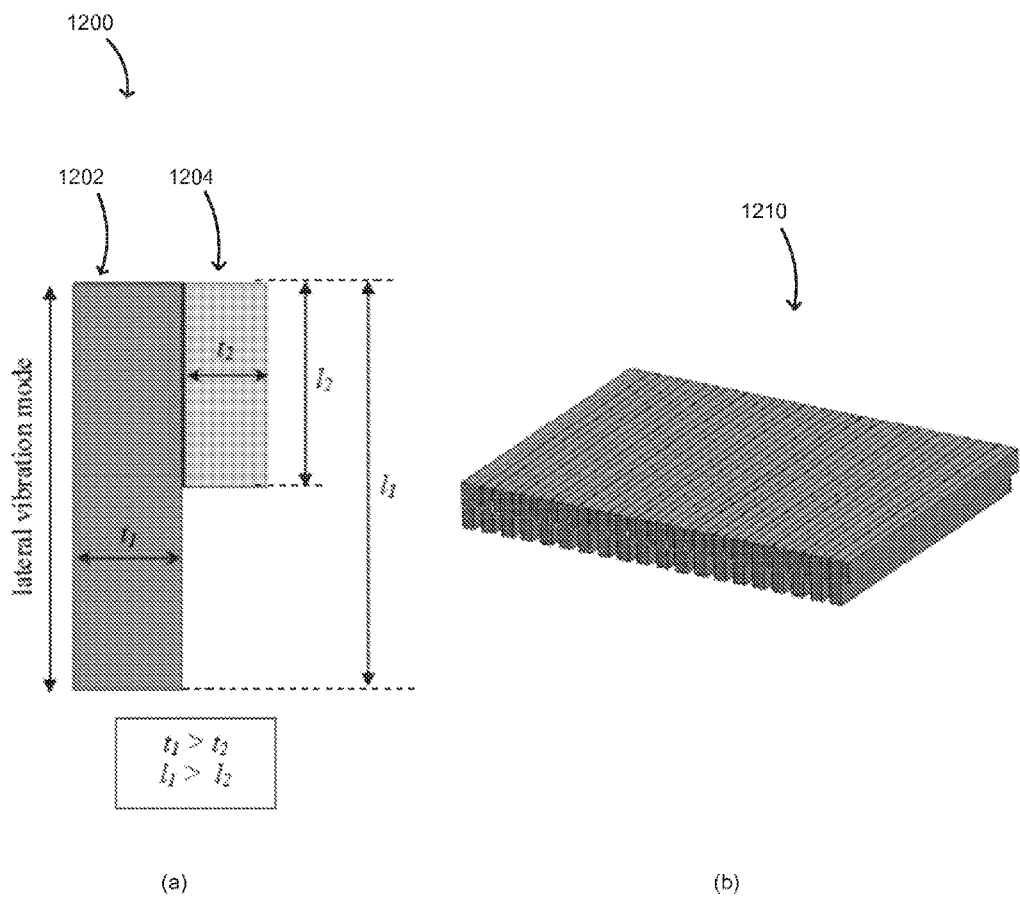
FIG. 12 illustrates an example of a dual-frequency 2-layer PZT transducer with lateral vibration mode. (a) construction of an individual element in the dual frequency transducer, and (b) fully assembled dual frequency transducer.

FIG. 12(*b*) shows a fully assembled dual frequency transducer array 1210. In other embodiments, this can be extended to any number of frequencies and all transducer and array configurations and geometries. Stacking, packing and distributing the array elements in the face or body of the transducer array is also possible.

Figure 13:
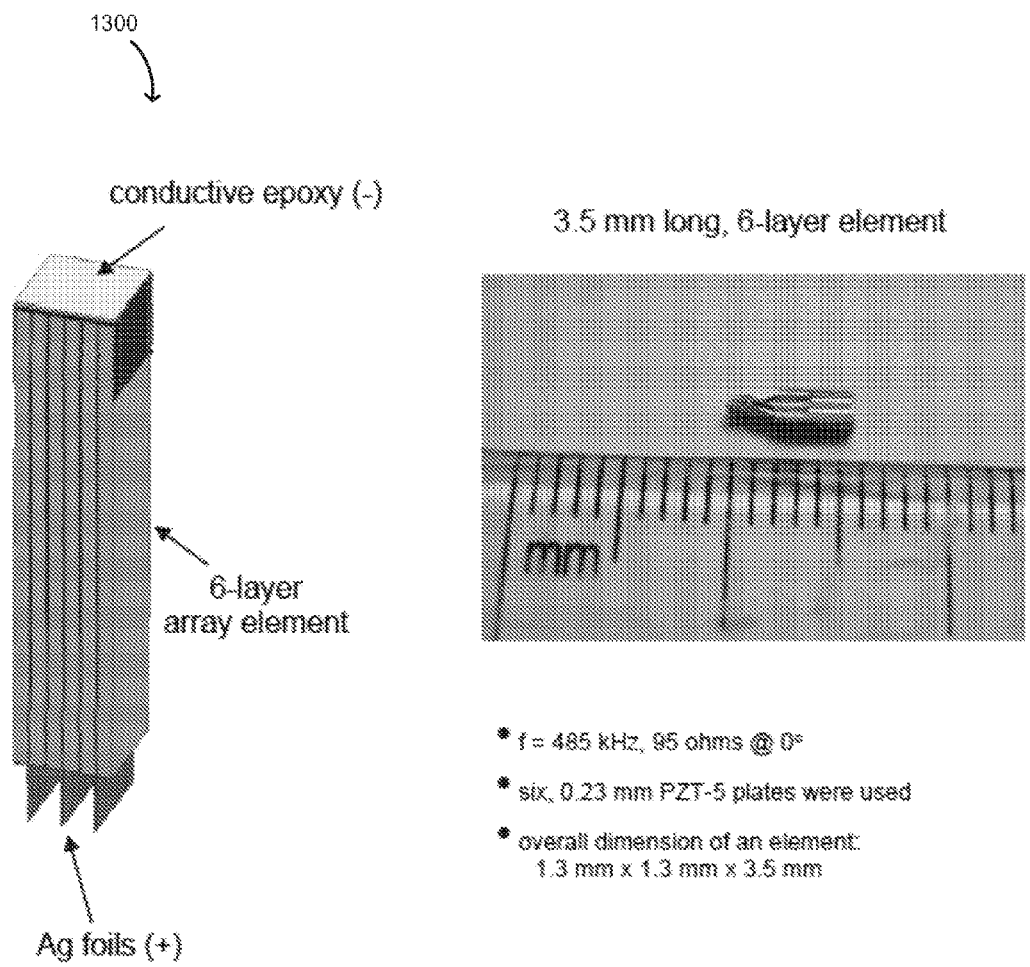
FIG. 13 illustrates an exemplary schematic of the construction of a six layer transducer element for a 2-dimensional array, and shows an actual 6 layer element.
Figure 14:
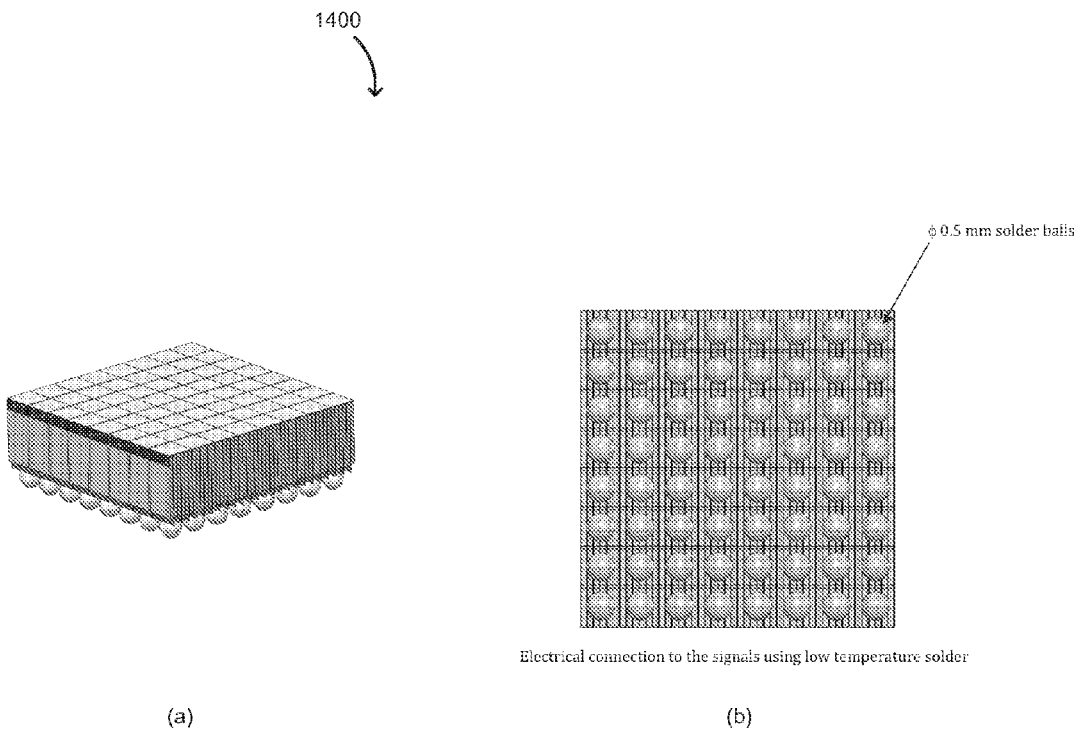
FIG. 14 illustrates (a) a sketch of a 8×8 2D array made using six layer elements; (b) a bottom view of the array showing electrical connectors using low temperature solder balls; and (c) a photograph of a 8×8 2D array.

The same method for making the above systems can, again, be extended to 1.5 or 2 dimensional arrays as shown in FIGS. 13 and 14, respectively.

FIG. 14(*a*) illustrates a perspective view of an exemplary 2D array showing its front (transducer/emission side) face having a plurality of rows and columns arranged thereon. Acoustic energy radiates outwardly from each driven element of the transducer generally normally away from the active face of the transducer. FIG. 14(*b*) illustrates the 2D array from its front (transducer/emitter) side. For 2D arrays 1400 the transducer element widths can be selected such that the complete multilayer element will be more or less square. Therefore thinner and a larger number of plates can be used to reach the desired impedance.

For an imaging array, its narrow bandwidth could be improved by adding acoustic impedance matching layers on the array's front surface or using a different backing material. The electrical-to-acoustic power conversion efficiency of the HIFU array can be easily increased using more transducer layers in the element design. This transducer structure is fully scalable and therefore it is expected that even high frequency imaging arrays up to and beyond 100 MHz can be constructed.

The invention claimed is:

1. An ultrasound transducer element comprising:
   a piezoelectric stack comprising an even number of piezoelectric layers stacked along a first direction, said piezoelectric stack comprising a pair of outer electrodes formed on respective outer surfaces thereof, wherein each pair of adjacent piezoelectric layers within said piezoelectric stack are separated by, and mutually contact, a respective common electrode provided therebetween such that said outer electrodes and said common electrodes form a set of electrodes, each adjacent pair of electrodes having a respective piezoelectric layer provided therebetween;
   wherein odd-numbered electrodes, counted from a given side of said piezoelectric stack, are connected in parallel to form a common ground electrode, and even-numbered electrodes are connected in parallel to form a common signal electrode;
   such that, upon application of an electrical driving signal between said common ground electrode and said common signal electrode at a frequency associated with a lateral mode coupled resonance of said piezoelectric stack, lateral mode coupling causes said piezoelectric stack to be mechanically responsive along a second direction that is perpendicular to the first direction, thereby producing ultrasound emission along the second direction through an emitting surface of said ultrasound transducer element located at a first end of said ultrasound transducer element; and
   wherein said even-numbered electrodes extend from a second end of said piezoelectric stack in direction parallel to the second direction and are brought into electrical communication beyond the distal end of said piezoelectric stack.

2. The ultrasound transducer element according to claim 1 wherein said even-numbered electrodes that extend from said second end contact low-temperature solder, thereby forming said common signal electrode.

3. The ultrasound transducer element according to claim 1 wherein said common ground electrode extends parallel to said emitting surface at said first end of said ultrasound transducer element.

4. The ultrasound transducer element according to claim 1 wherein said piezoelectric layers have equal lengths along the second direction.

5. The ultrasound transducer element according to claim 1 wherein two or more of said piezoelectric layers have different lengths along the second direction, such that said piezoelectric layers having different lengths resonate at different frequencies via lateral mode coupled excitation.

6. The ultrasound transducer element according to claim 5 wherein the different lengths are selected such that said ultrasound transducer element exhibits a combined wideband operation.

7. The ultrasound transducer element according to claim 1 wherein said piezoelectric stack has a square cross-sectional shape perpendicular to the second direction.

8. A phased-array ultrasound device comprising a one-dimensional array of ultrasound transducer elements formed according to claim 1.

9. A phased-array ultrasound device comprising a two-dimensional array of ultrasound transducer elements formed according to claim 1, wherein said ultrasound transducer elements are arranged such that said common signal electrodes are individually addressable at a back side of said two-dimensional array, wherein said back side is associated with said second ends of said ultrasound transducer elements.

10. The phased-array ultrasound device according to claim 9 wherein said ultrasound transducer elements are arranged such that said outer electrodes provide electrical connections among said common ground electrodes of said ultrasound transducer elements.

* * * * *